US006352695B1

(12) United States Patent
Budowsky et al.

(10) Patent No.: US 6,352,695 B1
(45) Date of Patent: *Mar. 5, 2002

(54) METHODS AND COMPOSITIONS FOR THE SELECTIVE MODIFICATION OF NUCLEIC ACIDS

(75) Inventors: Edward I. Budowsky, Brookline; Samuel K. Ackerman, Weston; Andrei A. Purmal, Waltham; Clark M. Edson, Somerville, all of MA (US)

(73) Assignee: V.I. Technologies, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/943,643

(22) Filed: Oct. 3, 1997

(51) Int. Cl.$^7$ .................. A61K 39/12; A61K 35/14; C12N 7/00
(52) U.S. Cl. .................. 424/204.1; 424/211.1; 424/229.1; 424/232.1; 424/233.1; 424/529; 435/235.1; 435/236; 435/238; 514/642; 514/183
(58) Field of Search ............ 424/184.1, 204.1, 424/211.1, 229.1, 232.1, 233.1, 529; 435/235.1, 236, 238; 514/642, 183; 604/4, 403

(56) References Cited

U.S. PATENT DOCUMENTS

| 3,492,289 A | 1/1970 | Symm et al. ............... 260/239 |
| 4,036,952 A | 7/1977 | Bauer et al. |
| 4,058,599 A | 11/1977 | Bauer et al. |
| 4,098,726 A | 7/1978 | Wagner et al. ............... 528/403 |
| 4,161,581 A | 7/1979 | Wagner et al. ............... 525/411 |
| 4,206,295 A | 6/1980 | Wagner et al. ............... 525/410 |
| 4,784,992 A | 11/1988 | Reiner ............... 514/77 |
| 4,841,023 A | 6/1989 | Horowitz ............... 530/351 |
| 5,000,951 A | 3/1991 | Bass et al. ............... 424/89.9 |
| 5,055,485 A | 10/1991 | Geacintov et al. ............... 514/449 |
| 5,120,649 A | 6/1992 | Horowitz et al. ............... 435/173 |
| 5,232,844 A | 8/1993 | Horowitz et al. ............... 435/173.1 |
| 5,374,424 A | 12/1994 | Kelsey et al. ............... 424/202.1 |
| 5,418,130 A | 5/1995 | Platz et al. ............... 435/2 |
| 5,559,250 A | 9/1996 | Cook et al. ............... 549/282 |
| 5,698,432 A | 12/1997 | Oxford ............... 435/236 |
| 6,136,586 A | * 10/2000 | Budowsky ............... 435/238 |

FOREIGN PATENT DOCUMENTS

| EP | 0612532 A2 | 8/1994 |
| JP | 53-82735 | 7/1978 |
| RO | 101400 | 4/1992 |
| SU | 1768636 A1 | 10/1992 |
| SU | 594771 A1 | 7/1993 |
| WO | WO 92/03157 | 3/1992 |
| WO | WO 92/04031 | 3/1992 |
| WO | WO 92/18161 | 10/1992 |
| WO | WO 96/39818 | 12/1996 |

OTHER PUBLICATIONS

Bahnemann, "Inactivation of viruses in serum with binary ethyleneimine " *J. Clin. Microbiol.* 3:209–210 (1975).

Bahnemann, "Inactivation of viral antigens for vaccine preparation with particular reference to the application of binary ethylenmine" *Vaccine* 8:299–303 (1990).

Bieniarz et al., "A facile, high–yielding method for the conversion of halides to mercaptans" *Tetrahedron Lett.* 34:939–942 (1993).

Budowsky et al., "Inactivation of the phage MS2 infectivity by the action of ethyleneimines" *Biorg. Khim.* 11:989–991 (1985) (in Russian). English Abstract provided, 1 page.

Budowsky and Zalesskaya, "Principles of selective inactivation of viral genome. V. Rational selection of conditions for inactivation of the viral suspension infectivity to a given extent by the action of B–propiolactone" *Vaccine* 9:319–325 (1991).

Budowsky et al., "Principles of selective inactivation of the viral genome; dependence of the rate of viral RNA modification on the number of protonizable groups in ethyleneimine oligomer" *Vaccine Res.* 5:29–39 (1996).

Creech et al., "Antitumor and mutagenic properties of a variety of heterocyclic nitrogen and sulfur mustards" *Med. Chem.* 15:739–746 (1972).

Dermer and Ham, *Ethyleneimine And Other Aziridines*, Acad. Press, NY —London (1969), pp. 249–285.

Earley et al., "Reactions of ethylenimines. IX. The mechanisms of ring openings of ethylenimines in acidic solutions" *J. Am. Chem. Soc.* 80:3458–3462 (1958).

King, "Evaluation of different methods of inactivation of newcastle disease virus and avian influenza virus in egg fluids and serum" *Avian Diseases* 35:505–514 (1991).

Kochetkov and Budowsky eds., *Organic Chemistry of Nucleic Acids*, Part A, Plenum Press, London–New York, pp. 48–55 (1972).

(List continued on next page.)

Primary Examiner—Padmashri Ponnaluri
(74) Attorney, Agent, or Firm—Clark & Elbing, LLP

(57) ABSTRACT

Methods and compositions for selectively modifying nucleic acid molecules in biological compositions, including contacting the composition with an inactivating agent having the formula:

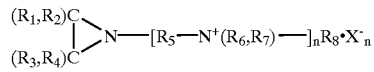

where each of $R_1$, $R_2$, $R_3$, $R_4$, $R_6$, $R_7$, and $R_8$ is, independently, H or a monovalent hydrocarbon moiety containing between 1 and 4 carbon atoms, inclusive, provided that $R_1$, $R_2$, $R_3$, $R_4$, $R_6$, $R_7$, and $R_8$ cannot all be H; $R_5$ is a divalent hydrocarbon moiety containing between 2 and 4 carbon atoms, inclusive; X is a pharmaceutically acceptable counter-ion; and n is an integer between 2 and 10, inclusive are disclosed.

15 Claims, No Drawings

OTHER PUBLICATIONS

Kostyanovskii et al., "Oligomers of azridines and N–beta–azridinoethylamides," Bull. Acad. Sci. USSR, Div. Chem. Sci. 37:2315–2325 (1989). (Translated from IzvestiyaAkademi Nauk SSSR, Seriya Khimicheskaya 11:2566–2575.).

Prodouz et al., "Inhibition of merocyanine 540–mediated photosensitization of platelets and viruses" *Transfusion* 31:415–422 (1991).

Race et al., "An experimental chemically inactivated HIV–1 vaccine induces antibodies that neutralize homologous and heterologous viruses" *Vaccine* 13:54–60 (1995).

Tanirbergenov et al., "Regularities of mutagenic and toxic effects of ethyleneimine and its oligomers. A comarative study in the automated system SOS–chromotest and in standard bacterial test systems" *Genetika* 24:763 (1988) (in Russian). English translation provided, 5 pages.

Thanei–Wyss, "Interaction of quaternary ammonium compounds with acetylcholinesterase: characteristics of the active site" Eur. J. Pharmacol., Mol. Pharmacol. Sect. 172:165–173 (1989).

Twomey et al., "Structure and immunogenicity of experimental foot–and–mouth disease and poliomyelitis" Vaccine 13:1603–1610 (1995).

Van Etten and Dolhum, "Effects of hydrogen–bond formation by phenols on the conformational equillibrium of trans–1,2–dimethyl–3–isopropylaziridine" J. Org. Chem. 33:3904–3907 (1968).

Wagner et al., "Approaches to the reduction of viral infectivity in cellular blood componets and single donor plasma" Transfusion Med. Rev. 5:18–32 (1991).

\* cited by examiner

METHODS AND COMPOSITIONS FOR THE SELECTIVE MODIFICATION OF NUCLEIC ACIDS

BACKGROUND OF THE INVENTION

This invention relates to methods and compositions for the selective modification of nucleic acids in biological compositions.

Transmission of viral diseases (e.g., hepatitis A and B, acquired immunodeficiency syndrome (HIV), cytomegalovirus infections) by blood or blood products is a significant problem in medicine. While donor selection criteria and screening of donor blood for viral markers helps reduce the transmission of viruses to recipients, screening methods are incomplete or less than 100% sensitive, as most are directed to only a few discrete viruses. Even in such cases, their sensitivity is insufficient. In addition, other biological compositions, e.g., mammalian and hybridoma cell lines, products of cell lines, milk, colostrunm and sperm, can contain infectious viruses.

It is desirable to inactivate any virus contained in donor blood, blood products, or other biological compositions. At the same time, it is important to leave the structure and function of valuable constituents, such as red blood cells, platelets, leukocytes, and plasma biopolymers, such as proteins and polysaccharides relatively unchanged.

In addition, it is often unknown whether compositions containing blood, blood products, or products of mammalian cells contain infectious viruses. In this case it would be valuable to have compositions and methods to treat such compositions to inactivate any infectious viruses present.

Furthermore, the manufacture of maximally safe and effective killed vaccines for human or veterinary use requires methods which completely and reliably render live microorganisms, e.g., viruses and bacteria, noninfectious ("inactivated") but which have minimal effects on their immunogenicity. Methods typically used for the inactivation of viruses, such as those useful in the preparation of viral vaccines, generally alter or destroy the function and structure of cells, cell components, proteins and other antigens.

Current inactivation methods, including the use of formalin, beta-propiolactone, and ultraviolet radiation, have been developed empirically, with little basis in fundamental chemical or structural principles. For example, ethyleneimine monomers have been used to inactivate the foot-and-mouth disease virus (Russian patent no. SU 1915956). Ethyleneimine monomers have also been used to inactivate Mycoplasma and Acholeplasma (WO 92/18161) and avian infections (Romania patent no. RO 101400). Binary ethyleneimine (i.e., ethyleneimine monomer generated by a combination of two reagents) has been used for the inactivation of feline enteric coronavirus, FECV, (EP 94200383). Polyethyleneimine has been used as a plant virus control agent (JP 7882735). The foregoing methods and compounds modify microorganisms, such as viruses and bacteria, nonspecifically, and are difficult to standardize and apply reproducibly.

In addition, ignorance of which chemical alterations render the microorganism noninfectious makes the process difficult to apply reproducibly. Periodic outbreaks of disease resulting from inadequate inactivation or reversion following inactivation are the result. Major outbreaks of paralytic poliomyelitis, foot and mouth disease and Venezuelan equine encephalitis have occurred due to this problem.

In general, multiple components of the microorganism, including important surface antigenic determinants such as viral capsid proteins, are affected by currently used inactivating agents. These agents significantly modify not only nucleic acids but also other biopolymers such as proteins, carbohydrates and lipids, thereby impairing their function. Altered antigens or the inactivation of protective epitopes can lead to reduced immunogenicity and hence low potency (e.g., inactivated polio vaccine), to altered antigenicity and hence immunopotentiation of disease instead of disease prevention (e.g., respiratory syncytial virus and inactivated measles vaccines produced by formalin inactivation), or to the appearance of new antigens common to another killed vaccine prepared with the same inactivant.

For example, in the preparation of hepatitis B virus vaccine, it is common practice to heat preparations at temperatures in excess of 80° C. and to treat with formaldehyde. These treatments not only inactivate viral infectivity, but also damage proteins and other antigens. Carrier substances added to the vaccine as stabilizers also may be unintentionally modified, producing allergic reactions, as occurs with human serum albumin in rabies vaccine inactivated with beta-propiolactone.

The problems of inactivation of viruses in biological mixtures are distinct from the problems of inactivation of the viruses alone due to the co-presence of desirable biopolymers such as proteins, carbohydrates, and glycoproteins in the plasma. While it is possible to inactivate the hepatitis B virus by using agents such as formaldehyde or oxidizing agents, these methods are not suitable for the inactivation of viruses in blood, due to the observation that most of these inactivating agents impair the biological activity of biopolymers in plasma or cellular components of blood. For example, the use of ultraviolet light has been shown to inactivate viruses in a platelet concentrate. However, severe platelet damage resulted from higher doses. Beta-propiolactone reacts with nucleic acid and protein at similar rates; thus, while viruses can be inactivated, more than half of the factor VIII activity of plasma is lost.

Yet another problem is that some of the viruses contaminating blood or other biological fluids are contained within the cell, either as a fully formed virus, viral genome fragments, or viral nucleic acid integrated into the host genome. For instance, the HIV virus is contained within leukocytes. It is a special concern to be able to inactivate both cell-free and cell-contained forms of virus, while retaining the structural integrity of cells.

Problems may also exist in obtaining valuable biopolymers from non-blood sources since pathogenic viruses may also contaminate such compositions.

SUMMARY OF THE INVENTION

The invention features a method of selectively modifying nucleic acid molecules in a biological composition; the method includes the step of contacting the composition with an inactivating agent having the formula:

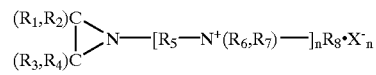

where each of $R_1$, $R_2$, $R_3$, $R_4$, $R_6$, $R_7$, and $R_8$ is, independently, H or a monovalent hydrocarbon moiety containing between 1 and 4 carbon atoms, inclusive, provided that $R_1$, $R_2$, $R_3$, $R_4$, $R_6$, $R_7$, and $R_8$ cannot all be H; $R_5$ is a divalent hydrocarbon moiety containing between 2 and 4 carbon atoms, inclusive; X is a pharmaceutically acceptable counter-ion; and n is an integer between 2 and 10, inclusive.

Preferably, $R_5$ is alkylene and each of $R_1$, $R_2$, $R_3$, $R_4$, R6, $R_7$, and $R_8$ is H or alkyl.

The invention further features a method for selectively inactivating a virus by contacting the biological composition with this inactivating agent, where the nucleic acid molecules are contained within an infectious vertebrate virus. This method may be used for both enveloped and non-enveloped viruses. The inactivated viruses can then be included in killed vaccines.

The invention also features a method for selectively modifying nucleic acids that are contained within a transforming DNA fragment, using this inactivating agent.

The invention also features a killed vaccine that includes an effective amount of inactivated vertebrate virus and a pharmaceutically acceptable carrier, where the inactivated vertebrate virus is made by a process of incubating the virus with an inactivating agent under viral inactivating conditions. The inactivating agent has the formula:

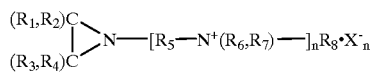

where each of $R_1$, $R_2$, $R_3$, $R_4$, $R_6$, $R_7$, and $R_8$ is, independently, H or a monovalent hydrocarbon moiety containing between 1 and 4 carbon atoms, inclusive, provided that $R_1$, $R_2$, $R_3$, $R_4$, $R_6$, $R_7$, and $R_8$ cannot all be H; $R_5$ is a divalent hydrocarbon moiety containing between 2 and 4 carbon atoms, inclusive; X is a pharmaceutically acceptable counter-ion; and n is an integer between 2 and 10, inclusive.

The inventions also features a blood-collecting device including a container for receiving blood or a blood fraction; the container includes an inactivating agent in an amount effective to inactivate viruses in the blood or fraction thereof received into the container. The inactivating agent has the formula:

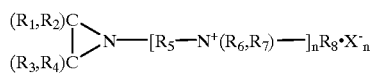

where each of $R_1$, $R_2$, $R_3$, $R_4$, $R_6$, $R_7$, and $R_8$ is, independently, H or a monovalent hydrocarbon moiety containing between 1 and 4 carbon atoms, inclusive, provided that $R_1$, $R_2$, $R_3$, $R_4$, $R_6$, $R_7$, and $R_8$ cannot all be H; $R_5$ is a divalent hydrocarbon moiety containing between 2 and 4 carbon atoms, inclusive; X is a pharmaceutically acceptable counter-ion; and n is an integer between 2 and 10, inclusive.

The invention further features a method of selectively modifying nucleic acid molecules in a biological composition; the method includes contacting the composition with an inactivating agent having the formula:

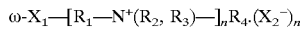

where $X_1$ is Cl or Br; $R_1$ is a divalent hydrocarbon moiety containing between 2 and 4 carbon atoms, inclusive; each of $R_2$, $R_3$, and $R_4$ is, independently, H or a monovalent hydrocarbon moiety containing between 1 and 4 carbon atoms, inclusive, provided that $R_2$, $R_3$, and $R_4$ cannot all be H when $R_1$ contains 2 carbon atoms; $X_2$ is a pharmaceutically acceptable counter-ion; and n is an integer between 2 and 10, inclusive. Preferably, $R_1$ is alkylene and each of $R_2$, $R_3$, and $R_4$ is H or alkyl.

The invention further features a method for selectively inactivating a virus by contacting the biological composition with this inactivating agent, where the nucleic acid molecules are contained within an infectious vertebrate virus. This method may be used for both enveloped and non-enveloped viruses. The inactivated viruses can then be included in killed vaccines.

The invention also features a method for selectively modifying nucleic acids that are contained within a transforming DNA fragment, using this inactivating agent.

The invention also features a killed vaccine including an effective amount of inactivated vertebrate virus and a pharmaceutically acceptable carrier, where the inactivated vertebrate virus is made by a process of incubating the virus with an inactivating agent under viral inactivating conditions; the inactivating agent has the formula:

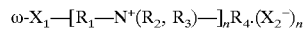

where $X_1$, is Cl or Br; $R_1$ is a divalent hydrocarbon moiety containing between 2 and 4 carbon atoms, inclusive; each of $R_2$, $R_3$, and $R_4$ is, independently, H or a monovalent hydrocarbon moiety containing between 1 and 4 carbon atoms, inclusive, provided that $R_2$, $R_3$, and $R_4$ cannot all be H when $R_1$ contains 2 carbon atoms; $X_2$ is a pharmaceutically acceptable counter-ion; and n is an integer between 2 and 10, inclusive.

The invention further features a blood-collecting device including a container for receiving blood or a blood fraction; the container includes an inactivating agent in an amount effective to inactivate viruses in the blood or fraction thereof received into the container. The inactivating agent has the formula:

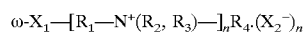

where $X_1$ is Cl or Br; $R_1$ is a divalent hydrocarbon moiety containing between 2 and 4 carbon atoms, inclusive; each of $R_2$, $R_3$, and $R_4$ is, independently, H or a monovalent hydrocarbon moiety containing between 1 and 4 carbon atoms, inclusive, provided that $R_2$, $R_3$, and $R_4$ cannot all be H when $R_1$ contains 2 carbon atoms; $X_2$ is a pharmaceutically acceptable counter-ion; and n is an integer between 2 and 10, inclusive.

The invention also features a nucleic acid inactivating agent having the formula:

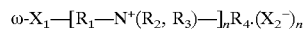

where $X_1$ is Cl or Br; $R_1$ is a divalent hydrocarbon moiety containing between 2 and 4 carbon atoms, inclusive; each of $R_2$, $R_3$, and $R_4$ is, independently, H or a monovalent hydrocarbon moiety containing between 1 and 4 carbon atoms, inclusive, provided that $R_2$, $R_3$, and $R_4$ cannot all be H when $R_1$ contains 2 carbon atoms; $X_2$ is a pharmaceutically acceptable counter-ion; and n is an integer between 2 and 10, inclusive. Preferably, $R_1$ is alkylene and each of $R_2$, $R_3$, and $R_4$ is H or alkyl.

The invention further features a method of selectively modifying nucleic acid molecules in a biological composition; the method includes the step of contacting the composition with an inactivating agent having the formula:

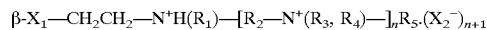

where $X_1$ is Cl or Br; each of $R_1$, $R_3$, $R_4$, and $R_5$ is, independently, H or a monovalent hydrocarbon moiety containing between 1 and 4 carbon atoms, inclusive; $R_2$ is a divalent hydrocarbon moiety containing 3 or 4 carbon atoms; $X_2$ is a pharmaceutically acceptable counter-ion; and n is an integer between 2 and 10, inclusive. Preferably, each of $R_1$, $R_3$, $R_4$, and $R_5$ is H or alkyl and $R_2$ is alkylene.

The invention further features a method for selectively inactivating a virus by contacting the biological composition with this inactivating agent, where the nucleic acid molecules are contained within an infectious vertebrate virus. This method may be used for both enveloped and non-enveloped viruses. The inactivated viruses can then be included in killed vaccines.

The invention also features a method for selectively modifying nucleic acids that are contained within a transforming DNA fragment, using this inactivating agent.

The invention also features a killed vaccine containing an effective amount of inactivated vertebrate virus and a pharmaceutically acceptable carrier, where the inactivated vertebrate virus is made by a process of incubating the virus with an inactivating agent under viral inactivating conditions; the inactivating agent has the formula:

$$\beta\text{-}X_1\text{—}CH_2CH_2\text{—}N^+H(R_1)\text{—}[R_2\text{—}N^+(R_3, R_4)\text{—}]_nR_5.(X_2^-)_{n+1}$$

where $X_1$ is Cl or Br; each of $R_1$, $R_3$, $R_4$, and $R_5$ is, independently, H or a monovalent hydrocarbon moiety containing between 1 and 4 carbon atoms, inclusive; $R_2$ is a divalent hydrocarbon moiety containing 3 or 4 carbon atoms; $X_2$ is a pharmaceutically acceptable counter-ion; and n is an integer between 2 and 10, inclusive.

The invention further features a blood-collecting device that includes a container for receiving blood or a blood fraction; the container includes an inactivating agent in an amount effective to inactivate viruses in the blood or fraction thereof received into the container. The inactivating agent has the formula:

$$\beta\text{-}X_1\text{—}CH_2CH_2\text{—}N^+H(R_1)\text{—}[R_2\text{—}N^+(R_3, R_4)\text{—}]_nR_5.(X_2^-)_{n+1}$$

where $X_1$ is Cl or Br; each of $R_1$, $R_3$, $R_4$, and R5 is, independently, H or a monovalent hydrocarbon moiety containing between 1 and 4 carbon atoms, inclusive; $R_2$ is a divalent hydrocarbon moiety containing 3 or 4 carbon atoms; $X_2$ is a pharmaceutically acceptable counter-ion; and n is an integer between 2 and 10, inclusive.

Finally, the invention features a nucleic acid inactivating agent having the formula:

$$\beta\text{-}X_1\text{—}CH_2CH_2\text{—}N^+H(R_1)\text{—}[R_2\text{—}N^+(R_3, R_4)\text{—}]_nR_5.(X_2^-)_{n+1}$$

where $X_1$ is Cl or Br; each of $R_1$, $R_3$, $R_4$, and $R_5$ is, independently, H or a monovalent hydrocarbon moiety containing between 1 and 4 carbon atoms, inclusive; $R_2$ is a divalent hydrocarbon moiety containing 3 or 4 carbon atoms; $X_2$ is a pharmaceutically acceptable counter-ion; and n is an integer between 2 and 10, inclusive. Preferably, each of $R_1$, $R_3$, $R_4$, and $R_5$ is H or alkyl and $R_2$ is alkylene.

"INACTINE™" refers to compounds of the invention having (1) an aziridino moiety or a halo-hydrocarbon-amine moiety, and (2) two or more nitrogen atoms separated by hydrocarbon moieties. These compounds are also referred to as "inactivating agents," or "selective inactivating agents."

An inactivating agent has "selectivity" for nucleic acids or "selectively" reacts with nucleic acids if the comparative rate of reaction of the inactivating agent with nucleic acids is greater than the rate of reaction with other biological molecules, e.g., proteins, carbohydrates or lipids.

"Nucleic acid" refers to both single and double stranded DNA and RNA.

"Biological composition" refers to a composition containing or derived from cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascitic fluid, proteins induced in blood cells, and products produced in cell culture by normal or transformed cells (e.g., via recombinant DNA or monoclonal antibody technology). Biological compositions can be cell-free.

"Biopolymer" or "biological molecule" refers to any class of organic molecule normally found in living organisms including, for example, nucleic acids, polypeptides, post-translationally modified proteins (e.g., glycoproteins), polysaccharides, and lipids. Biopolymer-containing compositions include, for example, blood cell proteins, blood plasma, a blood plasma fractionation precipitate, a blood plasma fractionation supernatant, cryoprecipitate, cryosupernatant or portion or derivative thereof, serum, or a non-blood product produced from normal or transformed cells (e.g., via recombinant DNA technology).

"Inhibit the activity of a biopolymer" means to measurably decrease the function or activity of the biopolymer. The decrease in function or activity can be determined by any standard assay used to measure the activity of the particular biopolymer. For example, the inhibition of an enzyme (protein) or antigen activity can be determined by measuring changes in the rate of an enzymatic process or an immune response to the antigen using conventional assays. Another example of such inhibition is the inhibition of the genome replication, transcription, or translation of an RNA molecule that can be determined by measuring the amount of protein encoded by the RNA that is produced in a suitable in vitro or in vivo translation system.

"Inactivating," "inactivation," or "inactivate," when referring to nucleic acids, means to substantially eliminate the template activity of DNA or RNA, for example, by destroying the ability to replicate, transcribe or translate a message. For example, the inhibition of translation of an RNA molecule can be determined by measuring the amount of protein encoded by a definitive amount of RNA produced in a suitable in vitro or in vivo translation system. When referring to viruses, the term means diminishing or eliminating the number of infectious viral particles measured as a decrease in the infectious titer or number of infectious virus particles per ml. Such a decrease in infectious virus particles is determined by assays well known to a person of ordinary skill in the art.

"Viral inactivating conditions" refer to the conditions under which the viral particles are incubated with the selective inactivating agents of this invention, including, for example, time of treatment, pH, temperature, salt composition, and concentration of selective inactivating agent, so as to inactivate the viral genome to the desired extent. Viral inactivating conditions are selected from the conditions described below for the selective inactivation of viruses in biological compositions.

"Diminish infectivity by at least 20 logs by calculation" means that the decrease in the number of infectious particles is determined by calculation as described herein in Examples 5 and 6.

"Virus" refers to DNA and RNA viruses, viroids, and prions. Viruses include both enveloped and non-enveloped viruses, for example, poxviruses, herpes viruses, adenoviruses, papovaviruses, parvoviruses, reoviruses, orbiviruses, picornaviruses, rotaviruses, alphaviruses, rubivirues, influenza virus, type A and B, flaviviruses, coronaviruses, paramyxoviruses, morbilliviruses, pneumoviruses, rhabdoviruses, lyssaviruses, orthmyxoviruses, bunyaviruses, phleboviruses, nairoviruses, hepadnaviruses, arenaviruses, retroviruses, enteroviruses, rhinoviruses and the filoviruses.

"Vaccine" is used in its ordinary sense to refer to an agent that is effective to confer the necessary degree of immunity on an organism while causing no morbidity or mortality. Methods of making vaccines are, of course, useful in the study of the immune system and in preventing animal or human disease.

"Pharmaceutically acceptable" means relatively non-toxic to the animal to whom the compound is administered. "Pharmaceutically acceptable carrier" encompasses any of the standard pharmaceutical carriers, buffers and excipients such as water, and emulsions, such as oil/water or water/oil emulsions, and various types of wetting agents and/or adjuvants.

The methods and compositions of the present inventions provide advantages over other approaches to selectively modifying nucleic acids in the presence of other biomolecules, and in the presence of cells. As the inactivating agents described herein are selective for the nucleic acids that make up viruses, viruses can be selectively inactivated over the other molecules present.

Other features and advantages of the invention will be apparent from the following description and from the claims.

DETAILED DESCRIPTION

The invention features methods for selectively modifying nucleic acids in a biological composition by contacting the composition with an inactivating agent. The nucleic acids in the composition are chemically modified at rates much faster than those of the other biological molecules. The methods are therefore useful in any process in which the practitioner wishes to modify nucleic acids, while leaving other biological molecules relatively unchanged. For example, the methods can be used to inactivate viruses selectively.

The inactivating agents of the present invention include both aziridino compounds and halo-hydrocarbon-amine compounds.

The aziridino compounds have the formula:

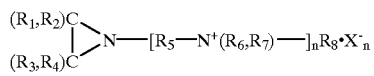

where each of $R_1$, $R_2$, $R_3$, $R_4$, $R_6$, $R_7$, and $R_8$ is, independently, H or a monovalent hydrocarbon moiety containing between 1 and 4 carbon atoms, inclusive, provided that $R_1$, $R_2$, $R_3$, $R_4$, $R_6$, $R_7$, and $R_8$ cannot all be H; $R_5$ is a divalent hydrocarbon moiety containing between 2 and 4 carbon atoms, inclusive; X is a pharmaceutically acceptable counter-ion; and n is an integer between 2 and 10, inclusive. These compounds can be prepared by the aziridine-initiated oligomerization of a halo-hydrocarbon-amino compound.

The halo-hydrocarbon-amine compounds can have the formula $\omega\text{-}X_1\text{---}[R_1\text{---}N^+(R_2, R_3)\text{---}]_nR_4 \cdot (X_2^-)_n$, where $X_1$ is Cl or Br; $R_1$ is a divalent hydrocarbon moiety containing between 2 and 4 carbon atoms, inclusive; each of $R_2$, $R_3$, and $R_4$ is, independently, H or a monovalent hydrocarbon moiety containing between 1 and 4 carbon atoms, inclusive, provided that $R_2$, $R_3$, and $R_4$ cannot all be H when $R_1$ contains 2 carbon atoms; $X_2$ is a pharmaceutically acceptable counter-ion; and n is an integer between 2 and 10, inclusive. These compounds can be prepared by the oligomerization of the corresponding halo-hydrocarbon-amino compounds.

Alternatively, these compounds can have the formula $\beta\text{-}X_1\text{---}CH_2CH_2\text{---}N^+H(R_1)\text{---}[R_2\text{---}N^+(R_3, R_4)\text{---}]_nR_5 \cdot (X_2^-)_{n+1}$, where $X_1$ is Cl or Br; each of $R_1$, $R_3$, $R_4$, and $R_5$ is, independently, H or a monovalent hydrocarbon moiety containing between 1 and 4 carbon atoms, inclusive; $R_2$ is a divalent hydrocarbon moiety having 3 or 4 carbon atoms; $X_2$ is a pharmaceutically acceptable counter-ion; and n is an integer between 2 and 10, inclusive. These compounds can be prepared by the aziridine-initiated oligomerization of an halo-hydrocarbon-amino compound, followed by conversion of the aziridino group to the corresponding halide compound.

The first step in viral inactivation according to the invention involves the physical association of an inactivating agent with nucleic acids through electrostatic interactions. The inactivating agents described above have multiple positively charged atoms, and are therefore oligocations. As oligocations, they have a high affinity for oligoanions. The association constant is proportional to the oligocation and oligoanion volume charge densities and therefore increases with the total average positive charge of the oligocation. Longer oligomers will have a higher total average positive charge, leading to an increase in their association constant with polynucleotides, for example with viral RNA. As nucleic acids are the major polyanionic components of viruses, this step results in the selective binding of the inactivating agents to viral nucleic acid, rather than to other virion components.

In addition, the distances between the positively charged nitrogen atoms of the inactivating agents is similar to the distances between the internucleotide phosphate groups (which are negatively charged) of polynucleotides.

In the case of aziridino compounds, the second step of viral inactivation is the protonation of the aziridino group. The reactivity of aziridines as electrophilic agents increases dramatically with the protonation of the aziridine nitrogen. Therefore, the form of these compounds protonated at the aziridino group is the more reactive form. The rates of usual electrophilic reactions of aziridines should be directly proportional to the concentration of their protonated forms in the complexes with polynucleotides.

The degree of protonation depends, in part, upon pH. In solution, the pK of the aziridino group decreases markedly as the total positive charge of the molecule increases. At a pH of about 7.0, the proportion of reactive aziridino groups in many inactivating agents is low. However, after association with a polyanion, the pK of the aziridino group increases significantly. Therefore, when the aziridino compound binds to a nucleic acid, the fraction of reactive aziridino groups increases locally.

The inactivating agents of this invention modify nucleic acids preferentially through the reaction of the aziridino group, or through the reaction of the terminal halo-hydrocarbon-amine group with the nucleic acid bases in polynucleotides. The action of these compounds on polynucleotides leads to amino-alkylation of nucleophilic groups in the nucleic acid bases.

Aziridines, like many electrophilic agents, modify nucleic acids preferentially at N7, N3, and N1 of purines and to a much lesser extent at N3 of pyrimidines. Template synthesis is arrested by alkylating agents primarily due to relatively slow opening of the imidazole ring of N7 alkylated purines, predominantly of guanine. For example, aziridine modifies guanosine to produce N7(aminoethyl)-guanosine which displays a much higher rate of imadozole ring opening than does N7-alkylguanosine.

In the absence of repair or recombination, the modification of the nucleotide bases blocks replication, transcription, and translation of the viral genome and renders the virus non-infectious. Virion coat proteins, however, are not modified to the same extent.

As the above discussion illustrates, it is the electrostatic interactions between the positively charged groups on the INACTINE™ and the negatively charged phosphate groups on the DNA and RNA backbones that result in the selectivity of the INACTINE™ for nucleic acids. The exact structures of the INACTINE™ are therefore not as critical as, for example, the structures of many pharmaceutically useful compounds. For example, a change in one of the R substituents from a methyl group to an ethyl group will not significantly affect an INACTINE™ compound's ability to selectively modify nucleic acids over other biomolecules.

What is important, however, is that the reactive part of the molecule (i.e., the aziridino group or the halo-hydrocarbon-amine group) remains reactive. For example, the aziridine ring will lose some of its reactivity if it is substituted by more than two hydrocarbon groups.

In addition, if the compounds contain hydrocarbon groups that have more than 4 carbon atoms, the compounds become lipophilic. Lipophilicity is undesired, as it will cause the agents to modify compounds such as proteins.

Aromatic rings are also undesirable substituents, as aromatic rings will intercalate in the DNA or RNA. The resulting change in the DNA or RNA structure disrupts the binding of the inactivating agents of the invention with the DNA or RNA.

The rate of modification of any virion component by traditional inactivating agents is usually considered a function of the average solution concentration of the agent. If a low-molecular-mass agent has a specific affinity for some polymer, however, the local concentration of agent near this polymer is higher than the average solution concentration of the agent and exponentially decreases with increased distances from the polymer. The selectivity of viral genome inactivation should be proportional to the difference in the local concentration of the agent near these biopolymers. Therefore, even a local increase in inactivating agent concentration near the genome should preferentially increase the modification rate of the genome.

However, as considered above, the formation of complexes between inactivating agents and polynucleotides should increase the extent of aziridino group protonation, and hence, the rate constant ($k_1$) of polynucleotide modification. Because of the exponential decrease in agent concentration with distance, at 1–2 nm away from the polymer the local concentration of agent is essentially the same as its average solution concentration. Obviously, the fraction of the reagent reactive form at this distance should be the same as in the free (non-associated) state in solution.

Therefore, the increase in the concentration of the inactivating agent in the vicinity of the polynucleotide, as well as the association of the inactivating agent with polynucleotide, should not affect the modification rate of the capsid component, especially their antigen-bearing regions at the surface of the virion, of a protein, or of other macromolecules in the surrounding solution.

The practitioner can determine the extent of alkylation of a viral nucleic acid by the extent of viral infectivity inactivation using various assays known to a person of ordinary skill in the art, such as determination of cytopathic effect (CPE) in tissue culture using serial dilutions of virus-containing mixtures introduced into susceptible cells, followed by incubation at 37° C. Modification of proteins, polysaccharides and glycoproteins with inactivating agents would lead to the introduction of additional positive charges. The extent of this biopolymer modification can be determined by means known in the art including, for example, isoelectric focusing, polyacrylamide gel electrophoresis, HPLC, and other forms of chromatography with detection by autoradiography or a suitable method.

All these data and considerations allow one to select an inactivating agent, with the desired polynucleotide affinity, leading to an increased rate of reaction and selectivity of the viral genome modification. Thus, even if the selectivity of the aziridine or halo-hydrocarbon-amino moiety is no better than the selectivity of other agents now used for preparation of whole virion killed vaccines, the significant increase in selectivity of the oligomeric inactivating agents makes negligible the effect of virion component modification on immunogenicity, stability and other virion properties.

Viruses can be inactivated by contacting a composition containing the virus with about 0.0001 M to about 0.015 M of an inactivating agent in a solution having an ionic strength of about 0.01 M to about 0.5 M, at a pH of about 6.5 to about 7.5, at a temperature of about 4° C. to about 45° C. The concentration of the inactivating agent depends, in part, on the number of positively charged atoms in the molecule. The selection of pH depends, in part, on the stability of the virion. The salts used can be any of those normally used in biochemical applications, including sodium, potassium, acetate, and so on. The practitioner can adjust the pH of the solution using many buffers customarily used in the art to handle biopolymers or cells, such as acetate, HEPES, MOPS, and so forth. The practitioner can also adjust other factors such as concentration of the reactants, temperature, and time of incubation. It should be kept in mind, however, that the reaction rate is dependent upon the ionic strength of the solution.

Experimentally, a decrease in infectivity can be measured to at least about "6 logs" in a cell- or biopolymer-containing composition. This means that the virus is inactivated to the extent determined by infectivity studies, where that virus is present in the untreated serum in such a concentration that even after dilution to $10^6$, viral activity can be measured. When a specific virus cannot be produced to a titer of $10^6$, inactivation is determined by direct quantitation measured up to the titer of virus produced. Alternatively, such a decrease in the number of infectious virus particles is determined by calculation as described herein to the extent of at least about "20 logs" based upon a kinetic description of the inactivation process based on a precise experimental determination of the infectivity of the viral suspension during inactivation while taking into account chemical, physical and biological factors affecting inactivation kinetics.

The inactivated viruses are made by a process of treating viruses under viral inactivating conditions effective to diminish infectivity to a desired extent (to at least about 6 logs by direct measurement or to at least 20 logs by calculation as described herein).

As described above, the inactivating agents of the invention can be used to selectively inactivate viruses in biological composition. In addition, the inactivating agents of the invention can be used to selectively modify nucleic acids that are contained within a transforming DNA fragment, for example, DNA from a polyoma virus.

Killed vaccines can be made by contacting a virus with a selective inactivating agent under viral inactivating conditions. The viral inactivating conditions are selected from the methods described above for modifying viral, bacterial or other nucleic acids. In general, virus at a titer of about $10^7$ to $10^8$ units per ml is incubated with inactivating agent at about pH 6.5 to about pH 7.5, in a solution having an ionic strength of less than about 0.5 M at about 4° C. to about 40° C. The time of treatment (i.e., the end point of inactivation) depends on the structure and composition of the particular virus, temperature of incubation, ionic strength, and the number of protonizable or positively charged groups in the inactivating agents. However, kinetic studies indicate that depending on pH and the virus to be inactivated, incubation time could be as little as a few seconds, and also can be about 1 hour, 5 hours, 50 hours, 100 hours 300 hours or 500 hours. The killed virus can be used directly in vaccine formulations, or lyophilized in individual or multiple dose containers for subsequent mixture with the pharmaceutically acceptable carrier. Methods of preparing vaccines are well known in the art and can be found, for example, in *Vaccines* (Slorein, G. Martance, E. eds) Second edition 1994, Saunders Harcourt-Brace, Phil, Toronto.

The vaccines of this invention are useful in the prevention of animal or human disease. Vaccines capable of conferring the desired degree of immunity will, of course, contain an amount of inactivated virus effective to evoke an immune response. In the preparation of killed vaccines, the sample of virus is incubated with the selective inactivating agents of this invention in amounts and under such conditions to inactivate the virus while retaining immunogenicity.

The vaccine can be administered in an adjuvant, i.e., a substance that potentiates an immune response when used in conjunction with an antigen. The vaccine can be given in an immunization dose. An immunization dose is an amount of an antigen or immunogen needed to produce or enhance an immune response. The amount will vary with the animal and immunogen or antigen or adjuvant but will generally be less than about 1000 µg per dose. The immunization dose is easily determined by methods well known to those skilled in the art, such as by conducting statistically valid host animal immunization and challenge studies. See, for example *Manual of Clinical Immunology*, H. R. Rose and H. Friedman, American Society for Microbiology, Washington, D.C. (1980).

Suitable pharmaceutical carriers and their formulations are described in Martin, *Remington's Pharmaceutical Sciences*, $91^{th}$ Ed. (Mack Publishing Co., Easton 1995). Such compositions will, in general, contain an effective amount of the compound together with a suitable amount of carrier so as to prepare the proper dosage form for proper administration to the subject.

The particular dosage of the vaccine to be administered to a subject will depend on a variety of considerations including the nature of the virus, the schedule of administration, the age and physical characteristics of the subject, and so forth. Proper dosages may be established using clinical approaches familiar to the medicinal arts.

Methods of treating cell- or biopolymer-containing compositions or preparing killed vaccines are particularly useful in the inactivation of viruses already known in the art to be irreversibly inactivated by other alkylating agents, such as ethyleneimine monomer and β-propiolactone. Therefore, while the agents of this invention have broader use by virtue of their selectivity, in selecting viruses for the preparation of vaccines or biological products for decontamination, the practitioner is guided, in part, by experience in the art with other inactivating agents.

The methods and compositions of the present invention can also be used to inactivate blood-transmitted viruses, bacteria, or parasites in cell- or biopolymer-containing compositions in various contexts, e.g., in the hospital, laboratory, or as part of a kit. Since cell compositions also comprise a variety of proteins, the method of viral inactivation described herein is also applicable to protein fractions, particularly blood plasma protein fractions or purified blood products. These include, but are not limited to, fractions containing clotting factors (such as factor VIII and factor IX), serum albumin and/or immune globulins. The viral and bacterial inactivation may be accomplished by treating a protein fraction or purified protein with a selective inactivating agent as described herein.

The process of the invention can be combined with still other modes of inactivating viruses. For example, certain processes used in the preparation of medical products (e.g., chromatography in buffers of low pH, or storage of red blood cells in acidic solutions containing calcium chelating agents) may have incidental viral inactivating properties for selected, sensitive viruses, usually enveloped viruses.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

Without further elaboration, it is believed that one skilled in the art can, based on the description herein, utilize the present invention to its fullest extent. The following specific examples are, therefore, to be construed merely as illustrative, and not limitative of the remainder of the disclosure in any way whatsoever. Publications mentioned herein are hereby incorporated by reference.

EXAMPLES

Example 1

Preparation of $Cl-[CH_2-CH_2-N^+(CH_2CH_3)_2-]_3 \cdot Cl^-_3$

An approach to the synthesis of this compound is as follows. 2-diethylaminoethyl chloride hydrochloride is dissolved in an excess of pyridine. After stirring for 5 minutes at room temperature, chloromethane is added. After stirring for an additional 60 minutes, the reaction is quenched by pouring the reaction mixture into water. The two phases are separated, and the organic phase is washed with brine and dried over $Na_2SO_4$. The solvent is then removed in vacuo to yield a mixture of oligomers, including $Cl-[CH_2-CH_2-N^+(CH_2CH_3)_2-]_3 \cdot (OH)^-_3$. This compound is isolated chromatographically. Following chromatography, the compound is added dropwise to vigorously stirred and cooled (0° C.) concentrated HCl. The mixture is stirred for an additional 10 minutes, then poured into absolute ethanol and stirred 1–2 hours at −20° C. The reaction mixture is then filtered through a scintered glass funnel under vacuum. The solids are washed three times with absolute ethanol. The inactivating agent hydrohalide trimer $Cl-[CH_2-CH_2-N^+(CH_2CH_3)_2-]_3 \cdot Cl^-_3$ is then recrystallized from aqueous ethanol.

Example 2

Preparation of $Cl-[CH_2-CH_2-N^+[CH(CH_3)_2]_2-]_3CH_3 \cdot Cl^-_3$

An approach to the synthesis of this compound is as follows. This compound can be prepared as described in the preceding paragraph, by substituting 2-diisopropylaminoethyl chloride hydrochloride for the 2-diethylaminoethyl chloride hydrochloride.

Example 3

Preparation of β-Cl—CH$_2$CH$_2$—N$^+$H(n-B)—[CH$_2$CH$_2$CH$_2$—N$^+$(Me)$_2$—]$_3$CH$_3$.Cl$^-_4$ An approach to the synthesis of this compound is as follows. 3-dimethylaminopropyl chloride hydrochloride is shaken with a saturated solution of NaHCO$_3$. Methylene chloride is added to the solution, and the phases are separated. The organic phase is washed with brine and dried over Na$_2$SO$_4$. The solid Na$_2$SO$_4$ is removed by filtration to yield a solution of 3-dimethylaminopropyl chloride.

N-(n-butyl) aziridine is dissolved in methylene chloride. The solution of 3-dimethylaminopropyl chloride is added dropwise. When the addition is complete, chloromethane is added and the reaction mixture is stirred an additional 60 minutes. The reaction mixture is then poured into water, and the phases are separated. The organic phase is washed with brine and dried over Na$_2$SO$_4$. The solvent is removed in vacuo to yield the aziridino compound

which is purified chromatographically.

The aziridino compound is added dropwise to vigorously stirred and cooled (0° C.) concentrated HCl. The mixture is stirred for an additional 10 minutes, then poured into absolute ethanol and stirred 1–2 hours at –20° C. The reaction mixture is then filtered through a scintered glass funnel under vacuum. The solids are washed three times with absolute ethanol. The hydrohalide compound β-Cl—CH$_2$CH$_2$—N$^+$H(n-Bu)—[CH$_2$CH$_2$CH$_2$—N$^+$(Me)$_2$—]$_3$CH$_3$.Cl$^-_4$ is then recrystallized from aqueous ethanol.

Example 4

Preparation of

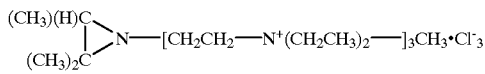

An approach to the synthesis of this compound is as follows. 2-methyl-2-butene is dissolved in anhydrous ether. 3-Chloroperoxybenzoic acid is added. The reaction mixture is stirred 30 minutes at room temperature, then poured into water. Brine is added, and the two phases are separated; the organic phase is washed with brine and dried over Na$_2$SO$_4$. The solvent is removed in vacuo to yield the epoxide.

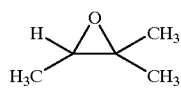

The epoxide is then dissolved in methylene chloride. Sodium azide is added to yield the corresponding azido alcohol compound.

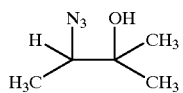

Triphenylphosphine is added to the reaction mixture to catalyze cyclization to the aziridine.

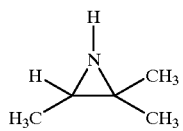

The reaction is quenched by pouring the reaction mixture into water. The two phases are separated; the organic phase is washed with brine and dried over Na$_2$SO$_4$. The solvent is removed in vacuo to yield the aziridine.

2-diethylaminoethyl chloride hydrochloride is shaken with a saturated solution of NaHCO$_3$. Methylene chloride is added to the solution, and the phases are separated. The organic phase is washed with brine, then dried over Na$_2$SO$_4$. The solid Na$_2$SO$_4$ is removed by filtration to yield a solution of 2-diethylaminoethyl chloride. The aziridine is added to this solution. After stirring for 30 minutes at room temperature, chloromethane is added. The reaction mixture is allowed to stir at room temperature for an additional 60 minutes, then quenched by pouring the reaction mixture into water. The phases are separated, and the organic phase is washed with brine and dried over Na$_2$SO$_4$. The solvent is removed in vacuo to yield a mixture of oligomers. The trimer

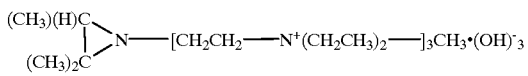

is isolated from this mixture chromatographically. Following chromatography, the compound is added dropwise to vigorously stirred and cooled (0° C.) concentrated HCl. The mixture is stirred for an additional 10 minutes, then poured into absolute ethanol and stirred 1–2 hours at –20° C. The reaction mixture is then filtered through a scintered glass funnel under vacuum. The solids are washed three times with absolute ethanol. The aziridino trimer is then recrystallized from aqueous ethanol.

Example 5

Bacteriophage Inactivation Kinetic Determination

Bacteriophage MS2 is prepared according to conventional procedure. Purification is performed by polyethylene glycol (PEG 6000, Serva) resedimentation or by chromatography on DEAE-SEPHADEX™ dextran A25 in a linear gradient of NaCl (0.02–1.0 M, 20 mM Tris HCl, pH 7.4). Purified phage are suspended in 0.15 M NaCl solution (2–10 mg per ml) and stored at 4° C. The infectivity of the phage suspension is determined by a conventional bilayer technique on a meat-peptone agar with *Escherichia coli* CA 180.

Aziridino inactivating agents are prepared as described above. Solutions of inactivating agents are prepared immediately before use by addition of a specified quantity of the compound to 0.15 M NaCl solution.

The pKa values of the protonizable groups of the aziridino inactivating agents in 0.15 M NaCl solution at 25° C. are calculated based on the results of the potentiometric titration by HCl using autotitrator TTT-60 (Radiometer) with a thermostatted cell compartment. The accuracy of the $pK_a$ value determination is no less than 0.05. The fraction of the reactive (protonized at the aziridine nitrogen) form of the agent (Q) is calculated by the following equation:

$$Q = \frac{1}{1 + 10^{pH - pK_i}}$$

where $pK_i$ is the $pK_a$ value of the aziridino group in the respective compound.

The total average positive charge of the molecule (p) is calculated using the following equation:

$$p = \sum_{0}^{n} n\delta (H_n A)^{n+}$$

where $\delta(H_n \cdot A)^{n+}$ is the fraction of the agent having positive charge n at the given pH value.

Before mixing, the virus-containing composition and freshly prepared solution of the selective inactivating agent are kept at 20° C. and the pH is adjusted by addition of dilute NaOH and HCl solutions. Aliquots of the reaction mixture incubated at 20° C. are taken at defined time intervals and after immediate 100-fold dilution used for the determination of the infectivity (titer). The effective rate constants of infectivity inactivation (k) are calculated by the following equation:

$$k = \frac{2.3}{At} \log S_0 / S_t$$

where A is the concentration (total or of the reactive fraction) of the agent; $S_0$ and $S_t$ are the infectivity (titer) of the suspension before and t min after the start of inactivation.

Example 6

Calculation of Inactivation Endpoint

The extent of infectivity reduction of the virus-containing composition may be controlled experimentally by at least about 6 orders of magnitude even if one increases the sample volume (within reasonable limits) and takes advantage of a series of successive passages. However, the production of safe killed antiviral vaccines requires that the infectivity of the original virus-containing composition be reduced by at least about 20 orders of magnitude. Therefore, in general, the safety of killed antiviral vaccines, cannot be determined solely by experiment and must be built into the method described herein. The safety can be assessed more meaningfully by calculation using a kinetic approach. This requires an accurate kinetic description of the inactivation conditions for the virus taking into account characteristics of the selective inactivating agent of this invention. Data can be obtained from the early (experimentally controlled) part of the survival curve.

An accurate kinetic description should be based on a precise determination of the infectivity of the viral suspension during inactivation. The skilled artisan should assure that the infectivity (titer) determination be accurate to assure determination of the inactivation rate constant and the minimal duration of the selective inactivating agent action ($t_1$). A reliable value of $t_1$ can be obtained using the kinetic approach described below, particularly when the survival curves provide a good kinetic description up to a specified degree of reduction in infectivity. Assuming the modification of the viral genome is not distorted by biological factors (such as DNA repair) and assuming that the formation of the first inactivating lesion, regardless of its position in the viral nucleic acid, blocks the complete replication of the genome, the survival curves for the virus during the action of the selective inactivating agent of this invention obey the following equation:

$$S = S_0 \exp(-Akt)$$

where $S_0$ and S are the infection titers of the virus-containing composition before and at time t after the start of the selective inactivating agent's action, A is the concentration of the selective inactivating agent and k is the rate constant for inactivation, i.e., modification of a nucleotide residue per genome.

Assuming the values of A and k are constant during inactivation, the survival curves are exponential. In this case, the inactivation duration required for a reduction of infectivity to a given extent can be calculated according to the following equation:

$$t_1 = [2.3/(Ak)] \log(S_0/S)$$

The endpoint of inactivation for any virus and any selective inactivating agent of this invention can be determined under inactivating conditions based on the data obtained from the initial part of the survival curve.

Example 7

Inactivation of Picornavirus.

Hepatitis A virus (genus enterovirus) and foot and mouth virus (aphthovirus) containing single-stranded RNA, positive chain, capsid containing only protein viruses are studied. The viruses are prepared according to conventional procedures including purification and determination of infectivity and stability. A selective inactivating agent of this invention is prepared as described above. The $pK_a$ values of the inactivating agents in a particular salt solution and at a particular temperature are determined.

Samples of the reaction mixture taken at appropriate time intervals are supplemented by thiosulfate (final concentration 0.1 M) for 30 minutes to quench the excess of the inactivating agent, and the infectivity titer of the reaction mixture is measured as described above. The time $t_1$ for reduction of the infectivity of these viruses by 20 orders of magnitude is calculated using the equation described above.

Example 8

Inactivation of Rhabdoviruses.

The inactivation of vesicular stomatitis virus (VSV) containing single-stranded RNA virus and a lipid-enveloped nucleocapsid is studied.

VSV is cultured in human A549 cells. Culturing and assay procedures are known to a person of ordinary skill in the art. Infectivity of VSV is assessed by endpoint, 10-fold serial dilutions in DMEM culture with 10% fetal calf serum. Each dilution is used to inoculate eight replicate wells of human A549 cells in 96 well microtiter plates. Virus induced cytopathology is scored after 72 hours of incubation at 37° C., in 5% $CO_2$. The reported virus titer is scored using known methods.

Cell-associated VSV is prepared by incubating a confluent monolayer of human A549 cells with 5 ml of $10^7$ $ID_{50}$/ml VSV in serum-free DMEM for 1 hour at 37° C., under 5% $CO_2$ in 150 $cm^2$ tissue culture flasks. The multiplicity of infection under these conditions is approximately 2.1 $TCID_{50}$/cell. To assess inactivation, the selective inactivating agent is added to the cell-associated virus in DMEM in 3 ml aliquots in polystyrene tubes. Aliquots of the reaction mixture are taken at definite time intervals and are supplemented with thiosulfate (final concentration 0.1M) for 30 minutes to quench the excess of the selective inactivating agent. Cells are removed by centrifugation and the infectivity titer of the supernatant and redispersed pellet is evaluated. The time $t_1$ for reduction of these viruses infectivity by 20 orders of magnitude is calculated using the equation described above.

The inactivation of cell free VSV added to whole blood ($5 \times 10^9$ red blood cells/ml) in the presence of selective inactivating agent is assessed. Virus infectivity is assessed as described herein. The time $t_1$ for reduction of these viruses infectivity by 20 orders of magnitude is calculated using the equation described above. Red blood cell structure and function is evaluated.

A control reaction, in which no inactivating agent is added, is run for comparison.

Example 9

Inactivation of Orthomyxoviridae.

The inactivation of influenza A virus, a single stranded fragmented RNA, negative chain, lipid enveloped capsid virus is evaluated. The virus is prepared according to conventional procedures including purification and determination of infectivity and stability. A selective inactivating agent of this invention is prepared as described above. The $pK_a$ values of the inactivating agent in a particular salt solution and at a particular temperature are determined. The influenza A virus and the selected viral inactivating agent is mixed at a particular pH, temperature and concentration using the conditions for the virus as set forth above. Virus infectivity is assessed as described herein. The time $t_1$ for reduction of these viruses infectivity by orders of magnitude is calculated using the equation described above.

Example 10

Inactivation of Human Immunodeficiency Virus

Human immunodeficiency virus (two copies of a single-stranded RNA genome, frequently mutated capsid proteins) is studied. HIV in either a cell-free or intracellular form is added to either whole blood or a red cell concentrate in a test tube. The selective inactivating agent is added and after processing of the samples HIV antigen measurements are made. Virus infectivity is assessed as described herein. The time $t_1$ for reduction of these viruses infectivity by 20 orders of magnitude is calculated using the equation described above.

Other embodiments are within the claims.
What is claimed is:

1. A method of selectively modifying nucleic acid molecules in a biological composition, said method comprising the step of contacting the composition with an inactivating agent having the formula:

$$\begin{array}{c}(R_1,R_2)C\\ (R_3,R_4)C\end{array}\!\!\!\!\!\!\diagdown\!\!N\!-\!\!-\![R_5\!-\!\!N^+(R_6,R_7)\!-\!\!-\!]_nR_8 \cdot X^-{}_n$$

wherein each of $R_1$, $R_2$, $R_3$, $R_4$, $R_6$, $R_7$, and $R_8$ is, independently, H or a monovalent hydrocarbon moiety containing between 1 and 4 carbon atoms, inclusive, provided that $R_1$, $R_2$, $R_3$, $R_4$, $R_6$, $R_7$, and R8 are not all H; $R_5$ is a divalent hydrocarbon moiety containing between 2 and 4 carbon atoms, inclusive; X is a pharmaceutically acceptable counter-ion; and n is an integer between 2 and 10, inclusive.

2. The method of claim 1, wherein $R_5$ is alkylene and each of $R_1$, $R_2$, $R_3$, $R_4$, $R_6$, $R_7$, and $R_8$ is, independently, H or alkyl.

3. The method of claim 1, wherein $R_5$ contains 3 carbon atoms.

4. The method of claim 1, wherein each of $R_1$, $R_2$, $R_3$, $R_4$, $R_6$, $R_7$, and $R_8$ is H or a linear alkyl group.

5. The method of claim 1, wherein at least two of $R_1$, $R_2$, $R_3$, and $R_4$ are H.

6. The method of claim 1, wherein at least three of $R_1$, $R_2$, $R_3$, and $R_4$ are H.

7. The method of claim 1, wherein X is selected from the group consisting of chloride, bromide, iodide, acetate, and tosylate.

8. The method of claim 1, wherein n is 2, 3 or 4.

9. The method of claim 1, wherein said biological composition contains at least one cell.

10. The method of claim 1, wherein said biological composition is selected from the group consisting of mammalian blood, purified or partially purified blood proteins, purified or partially purified blood components, blood cell proteins, blood plasma, platelet-rich plasma, a plasma concentrate, a precipitate from any fractionation of plasma, a supernatant from any fractionation of plasma, milk, saliva, serum, a cryoprecipitate, a cryosupernatant, a cell lysate, mammalian cell culture, mammalian cell culture medium, placental extracts, products of fermentation, ascitic fluid, and proteins induced in blood cells.

11. The method of claim 1, wherein said nucleic acid molecules are present within a transforming DNA fragment.

12. The method of claim 1, wherein said nucleic acid molecules are present within a virus that infects vertebrates.

13. The method of claim 12, wherein the virus is selected from the group consisting of poxviruses, herpes viruses, adenoviruses, rubiviruses, flaviviruses, coronaviruses, paramyxoviruses, morbilliviruses, pneumoviruses, vesiculoviruses, lyssaviruses, picornaviruses, orthomyxoviruses, bunyaviruses, phleboviruses, nairoviruses, hepadnaviruses, arenaviruses, retroviruses, enteroviruses, rhinovirus, and the filoviridae.

14. The method of claim 12, wherein the virus is an enveloped virus.

15. The method of claim 12, wherein the virus is a non-enveloped virus.

* * * * *